March 19, 1957 M. TANTAU Plant Pat. 1,580
ROSE PLANT
Filed June 7, 1956
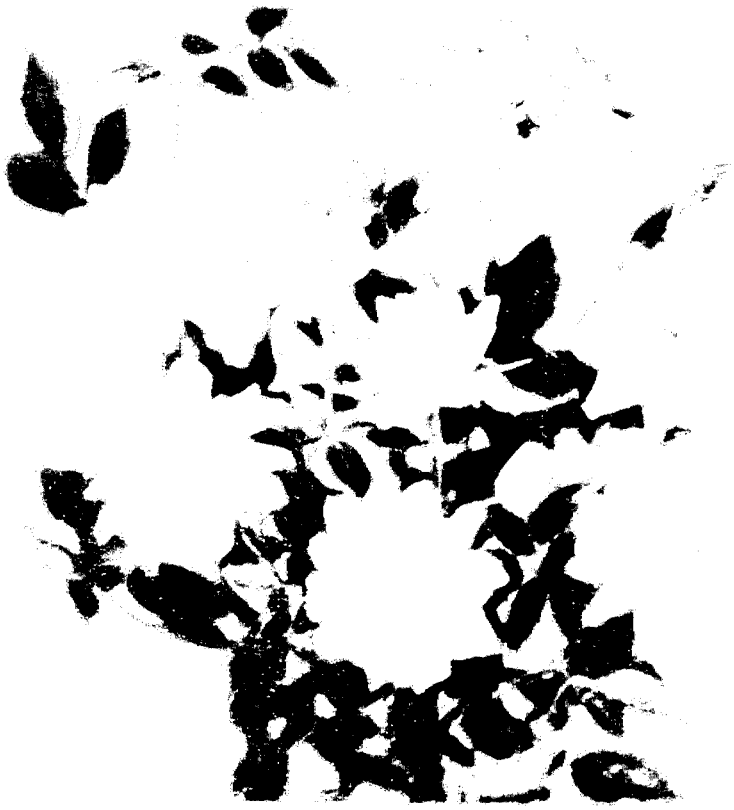
Inventor,
Mathias Tantau
By: Robb & Robb
Attorneys.

United States Patent Office

Plant Pat. 1,580
Patented Mar. 19, 1957

1,580

ROSE PLANT

Mathias Tantau, Uetersen, Holstein, Germany, assignor to Jackson & Perkins Company, Newark, N. Y., a corporation of New York Application June 7, 1956, Serial No. 590,080

1 Claim. (Cl. 47—61)

The present invention relates to a new and distinct variety of rose plant of the hybrid Chinensis minima class, which was originated by me by crossing the variety "Tom Thumb," which is known in Europe as "Peon" (U. S. Plant Patent No. 169), with the variety "Masquerade" (U. S. Plant Patent No. 975).

The primary objective of this breeding was to produce a new rose variety of the miniature type and which bears multi-colored flowers generally corresponding to those of the parent variety "Masquerade." This objective was fully achieved, along with other improvements, as evidenced by the following features which are outstanding in the new variety:

(1) The miniature size of the plant;

(2) The floriferousness of the plant, with virtually constant coverage of the plant with flowers;

(3) The miniature size of the flowers; and (4) The distinctive multi-colored flowers which range in progressive stages of development from Lemon Chrome to Rose Red on each plant.

The features noted above definitely distinguish my new variety from its parents, as well as from all other varieties of which I am aware, and asexual reproduction of the new variety by budding, as performed at Newark, New York, U. S. A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonable to make the same in a color illustration of this character.

The following is a detailed description of the new variety, with color terminology in accordance with Ridgway's Color Standards and Nomenclature:

Parentage: Seedling.

*Seed parents.*—"Tom Thumb" (known as "Peon" in Europe).

*Pollen parent.*—"Masquerade."

Classification:

*Botanic.*—Hybrid Chinensis minima.

*Commercial.*—Miniature.

*Flower*

(Observations made from specimens grown in a greenhouse at Newark, New York, U. S. A., in the early part of July and in the early morning.)

Blooming habit: Recurrent—continuous.

Bud:

*Size.*—Very small.

*Form.*—Ovoid; is not affected by wet or hot weather.

*Color.*—When sepals first divide—Rose Red, Plate 12. When sepals begin to unfurl—Martius Yellow, Plate 4, with a light overcast of Spectrum Red, Plate 1. When half-blown: inside of petals—Capucine Yellow, Plate 3, with upper half of petals Scarlet Red, Plate 1; reverse of petals—Light Cadmium, Plate 4, with outer edges of petals lightly overcast with Rose Red, Plate 12.

*Sepals.*—Branched, with "hood" above bud; curl back when petals begin to unfurl. Color: inside—Absinthe Green, Plate 31; outside—Yellowish Oil Green, Plate 5.

*Calyx.*—Color—Yellowish Oil Green, Plate 5. Shape—pear. Aspect—smooth. Odor when rubbed—none.

*Peduncle.*—Length — short. Aspect — smooth. Strength—erect; slender. Color—Jade Green, Plate 31.

*Opening.*—Opens to well; is not affected by adverse weather conditions.

Bloom:

*Size.*—Small. Average size when fully expanded—1 inch.

*Borne.*—Both singly and in irregular clusters.

*Stems.*—Short; normal strength.

*Form (when first open).*—Open. Permanence—retains its form to the end.

*Petalage.*—Double (full but open center). Number of petals under normal conditions—from 20 to 25.

*Color.*—First stage: center of flower — Lemon Chrome, Plate 4, lightly overcast with Light Cadmium, Plate 4; outer petals—Pinard Yellow, Plate 4, with edges of petals lightly overcast with Hermosa Pink, Plate 1; base of petals (aiglet)—Martius Yellow, Plate 4; inside of petals — Lemon Chrome, Plate 4; reverse of petals—Martius Yellow, Plate 4; general tonality from a distance—Lemon Chrome, Plate 4. Second stage: center of flower—Empire Yellow, Plate 4; outer petals—Orange Pink, Plate 2; base of petals (aiglet)—Pale Green Yellow, Plate 5; inside of petals—Pinard Yellow, Plate 4, lightly overcast with Empire Yellow, Plate 4; reverse of petals—Sulphur Yellow, Plate 5, lightly overcast with Baryta Yellow, Plate 4, with edges of petals La France Pink, Plate 1; general tonality from a distance—Pinard Yellow, Plate 4, lightly overcast with Orange Pink, Plate 2, on the outer rows of petals. Final stage: center of flower—Apricot Yellow, Plate 4, lightly overcast with Rose Red, Plate 12; outer petals—Rose Red, Plate 12; base of petals (aiglet)—Sulphur Yellow, Plate 5; inside of petals—Rose Red, Plate 12, lightly overcast with Pinard Yellow, Plate 4; reverse of petals—Rose Red, Plate 12, with lower half of petals lightly overcast with Baryta Yellow, Plate 4; general tonality from a distance—Rose Red, Plate 12, lightly overcast with Pinard Yellow, Plate 4, in the lower half of the petals.

*Discoloration.*—General tonality at end of first day—Lemon Chrome, Plate 4. Second day—Pinard Yellow, Plate 4, lightly overcast with Empire Yellow, Plate 4, with edges of outer rows of petals Orange Pink, Plate 2. Third day—Rose Red, Plate 12, lightly overcast with Pinard Yellow, Plate 4.

Petals:

*Texture.*—Thin; is not affected by wet or hot weather.

*Appearance.*—Inside—satiny. Outside—shiny.

*Form.*—Oval.

*Arrangement.* — Imbricated (regularly arranged shingle-like).

*Petaloids in center.*—Few; small.

*Persistence.*—Drop off cleanly.

*Fragrance.*—Slight. Nature—fruity (russet apple).

*Lasting quality.*—On the plant—long. As cut flower—long.

*Genital organs*

Stamens, anthers: Small; many; regularly arranged around styles. Color—Orange Buff, Plate 3.
Stamens, filaments (threads): Short. Color—Pinard Yellow, Plate 4.
Pollen: Color—Baryta Yellow, Plate 4.
Styles: Columnar; uneven length; short; thin.
Stigmas: Color—Martius Yellow, Plate 4.
Ovaries: All enclosed in calyx.
Hips: None.
Seeds: None.

*Plant*

Form: Bush.
Growth: Vigorous; compact; about 15 inches tall.
Foliage: Compound of 5 to 7 leaflets.
*Size.*—Small.
*Quantity.*—Normal.
*Color.*—New foliage: upper side—Light Bice Green, Plate 17, with serrations of Oxblood Red, plate 1; under side—Light Cress Green, Plate 31, lightly overcast with Carmine, Plate 1. Old foliage: upper side—Forest Green, Plate 17; under side—Rainette Green, Plate 31.
*Shape.*—Oval pointed.
*Texture.*—Upper side—leathery. Under side—smooth.
*Ribs and veins.*—Ordinary.
*Edge.*—Serrated (saw-toothed).
*Serration.*—Single; small.

*Leaf stem.*—Color—Absinthe Green, Plate 31. Under side—rough.
*Stipules.*—Short; bearded.
Wood:
*New wood.*—Color—Lettuce Green, Plate 5, lightly overcast with Carmine, Plate 1. Bark—smooth.
*Old wood.*—Color—Light Bice Green, Plate 17. Bark—smooth.
Thorns:
*Thorns.*—Quantity: on main stalks from base—few; on laterals from stalk—few. Form—short; straight; with narrow base. Color (when young)—Light Pinkish Cinnamon, Plate 29. Position—irregular.
*Prickles.*—Quantity: on main stalks—none; on laterals—none.
*Short needles.*—Quantity: on main stalks—none; on laterals—none.

I claim:

A new and distinct variety of rose plant of the miniature class, substantially as herein shown and described, characterized particularly as to novelty by the miniature size of both the plant and flowers, by its floriferousness and consequent substantially constant coverage of the plant with flowers, and by its multi-colored flowers which range in progressive stages of development from Lemon Chrome to Rose Red in general color tonality on each plant.

No references cited.